(12) United States Patent
Takefuji

(10) Patent No.: US 11,135,270 B2
(45) Date of Patent: Oct. 5, 2021

(54) METHOD FOR PREVENTING OR TREATING HEART FAILURE BY ADMINISTERING A MEDICAMENT CONTAINING AN ANTAGONIST OF CORTICOTROPIN RELEASING HORMONE RECEPTOR 2 (CRHR2)

(71) Applicant: RAQUALIA PHARMA INC., Aichi (JP)

(72) Inventor: Mikito Takefuji, Aichi (JP)

(73) Assignee: RAQUALIA PHARMA INC., Aichi (JP)

( * ) Notice: Subject to any disclaimer, the term of this patent is extended or adjusted under 35 U.S.C. 154(b) by 0 days.

(21) Appl. No.: 16/198,937

(22) Filed: Nov. 23, 2018

(65) Prior Publication Data

US 2019/0160151 A1    May 30, 2019

(30) Foreign Application Priority Data

Nov. 24, 2017    (JP) .............................. JP2017-226046

(51) Int. Cl.
| | |
|---|---|
| *A61P 9/04* | (2006.01) |
| *G01N 33/50* | (2006.01) |
| *A61K 38/16* | (2006.01) |
| *A61K 31/167* | (2006.01) |
| *A61K 38/22* | (2006.01) |
| *G01N 33/74* | (2006.01) |
| *C07K 14/575* | (2006.01) |
| *C07K 14/72* | (2006.01) |
| *C07K 14/00* | (2006.01) |

(52) U.S. Cl.
CPC ........ *A61K 38/2228* (2013.01); *A61K 31/167* (2013.01); *A61K 38/16* (2013.01); *A61P 9/04* (2018.01); *G01N 33/74* (2013.01); *C07K 14/001* (2013.01); *C07K 14/575* (2013.01); *C07K 14/57509* (2013.01); *C07K 14/72* (2013.01); *G01N 2333/726* (2013.01); *G01N 2500/02* (2013.01); *G01N 2800/325* (2013.01)

(58) Field of Classification Search
CPC .. A61K 38/2228; A61K 31/167; A61K 38/16; A61P 9/04
See application file for complete search history.

(56) References Cited

U.S. PATENT DOCUMENTS 6,593,838 B2 * 7/2003 Yue ..................... H01F 17/0006
257/531
6,953,838 B2 * 10/2005 Vale, Jr. ........... C07K 14/57509
530/350

OTHER PUBLICATIONS

Ruhmann et al, 1998. Proc Natl Acad Sci USA. 15264-156269.*
Pilbrow etal, 2016. Endocrinology. 157: 4865-4874, published on-line Oct. 18, 2016.*
Kang, M. et al., "G-Protein Coupled Receptor Signaling in Myocardium: Not for the Faint of Heart", Physiology, vol. 22, Jun. 2007, p. 174-184.
Capote, L.A. et al., "GPCR signaling and cardiac function", European Journal of Pharmacology, 763 (2015) p. 143-148.
Tamargo, J. et al, "Novel therapeutic targets for the treatment of heart failure", Nature Reviews Drug Discovery, vol. 10, July 2011, p. 536-555.
Takuma Tsuda et al., "Corticotropin releasing hormone receptor 2 exacerbates chronic cardiac dysfunction", J. Exp. Med. 2017, vol. 214, No. 7, pp. 1877-1888.
"Scientists identify protein linked to chronic heart failure", Rockfeller University Press, Public Release: May 26, 2017, https://www.eurekalert.org/pub_releases/2017-05/rup-sip052217.php.
"Scientists identify protein linked to chronic heart failure", Research Achievements, Nagoya University, May 30, 2017, Press Release, http://en.nagoya-u.ac/jp/research/activities/news/2017/05/scientists-identify-protein-li . . . .
The Chunichi Shimbun, Aug. 13, 2017 (in Japanese).

* cited by examiner

*Primary Examiner* — Zachary C Howard
(74) *Attorney, Agent, or Firm* — Wenderoth, Lind & Ponack, L.L.P.

(57) ABSTRACT

A medicament for preventing or treating heart failure containing an antagonist of the corticotropin releasing hormone receptor 2 as an active ingredient.

1 Claim, 14 Drawing Sheets

{Figure 1}
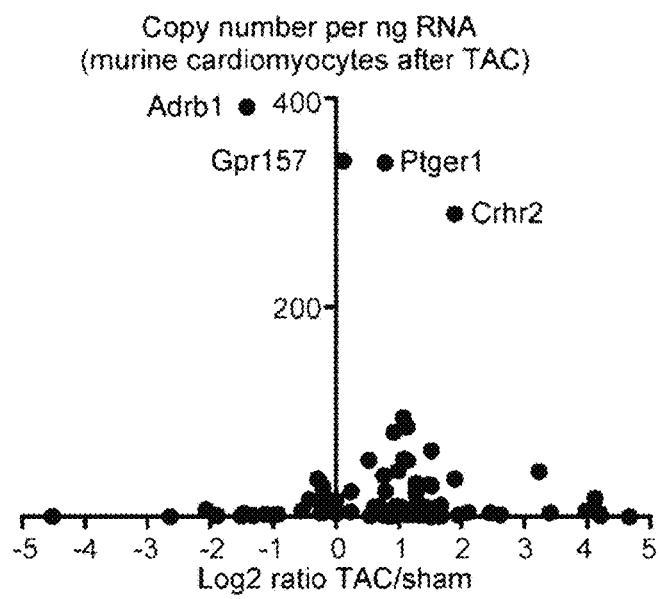
{Figure 2}
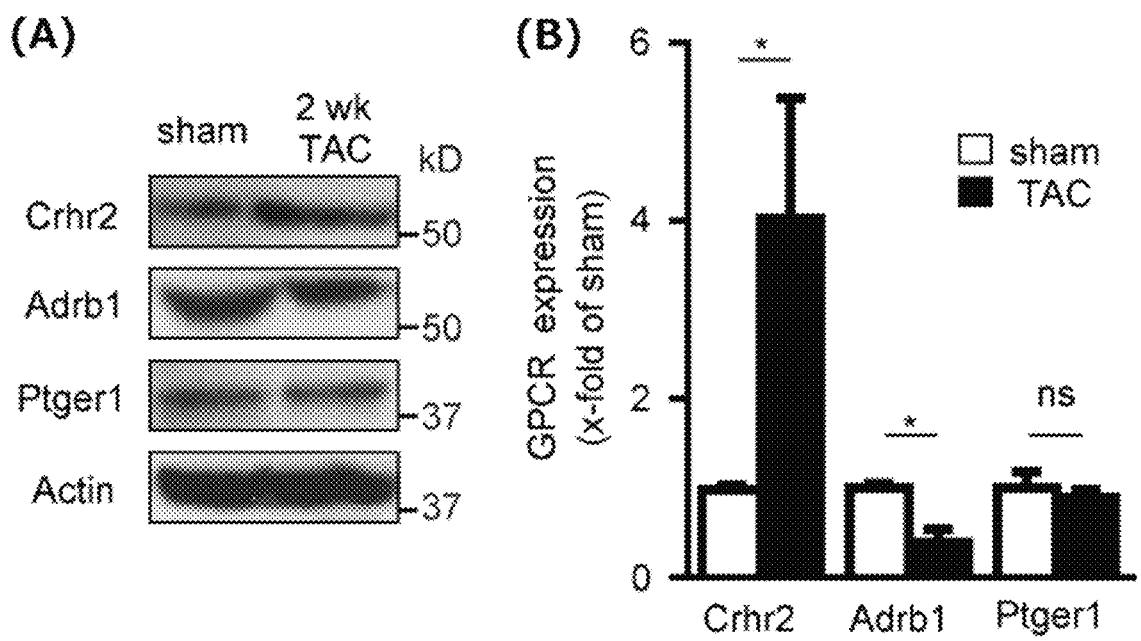

{Figure 3}
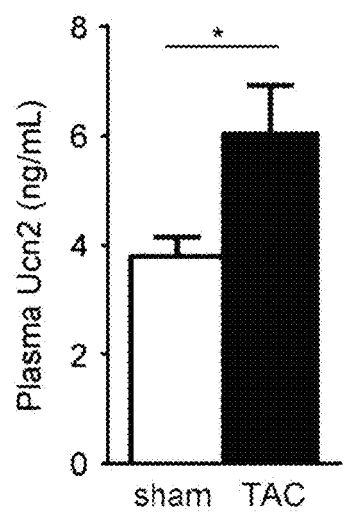
{Figure 4}
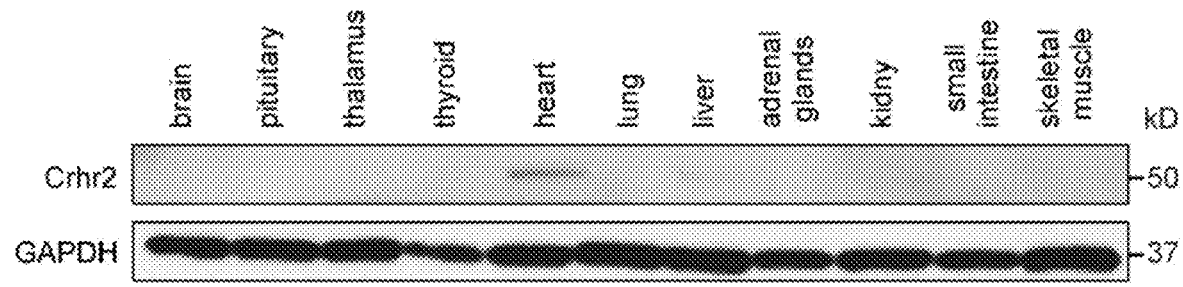

{Figure 5}
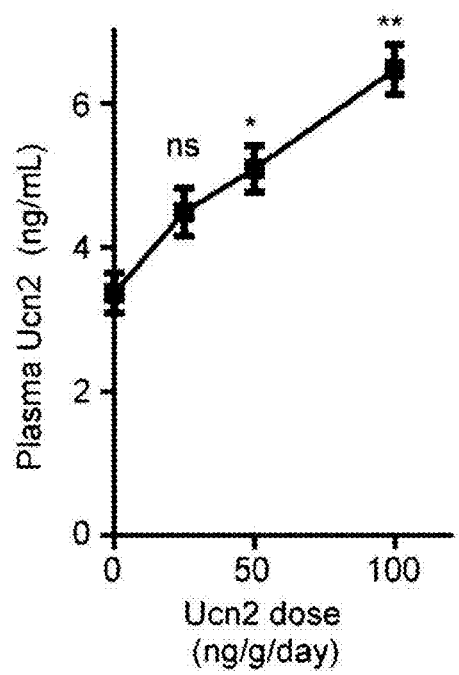

{Figure 6}
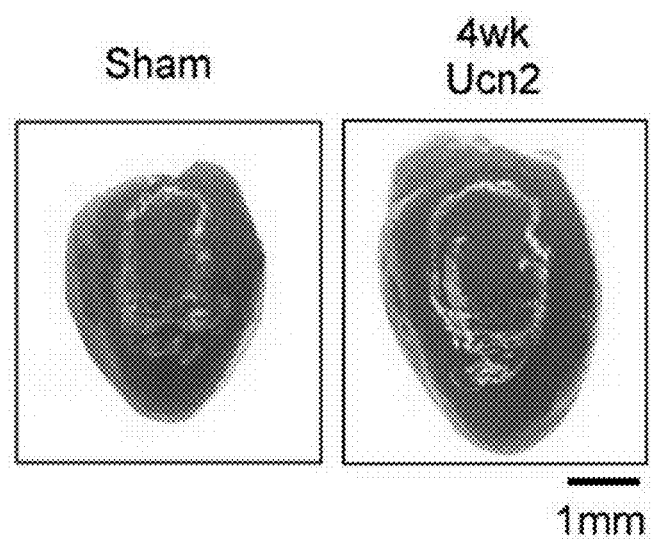
{Figure 7}
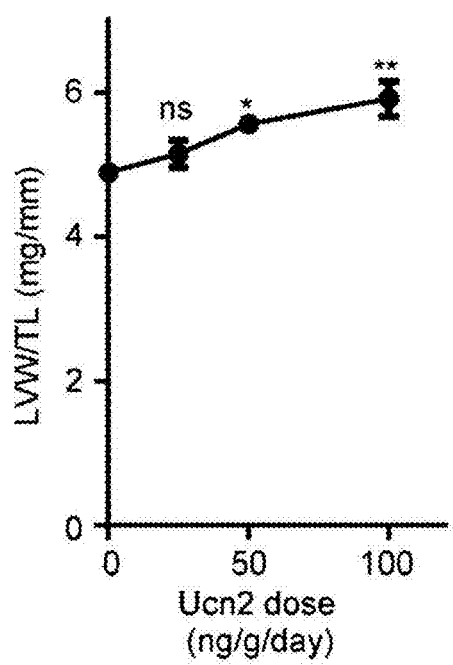

{Figure 8}
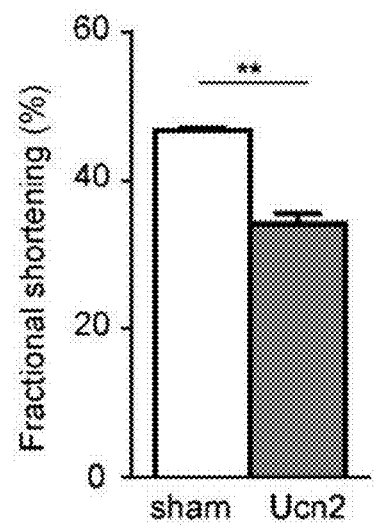
{Figure 9}
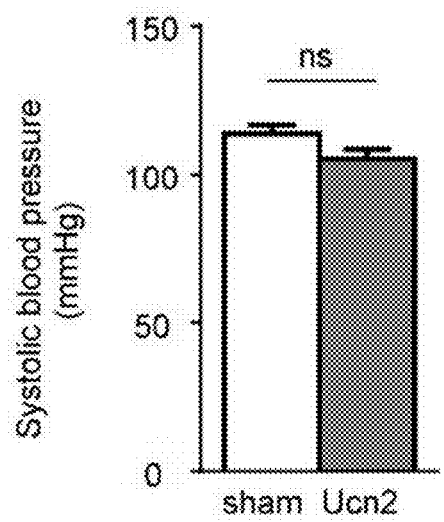

{Figure 10}
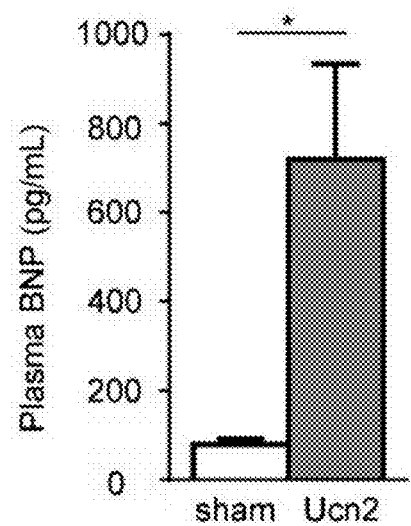
{Figure 11}
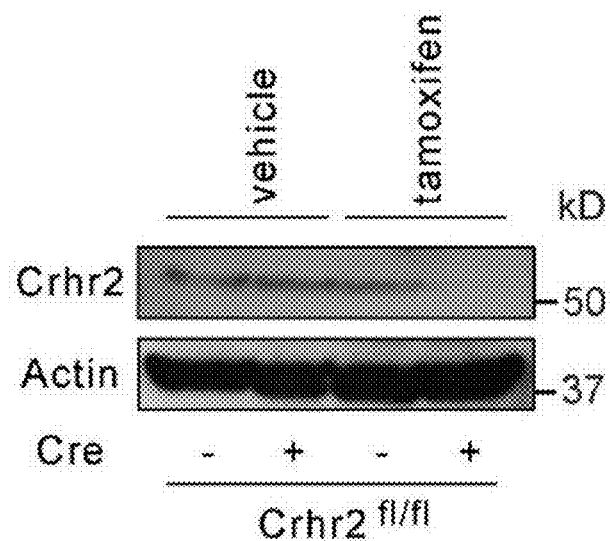

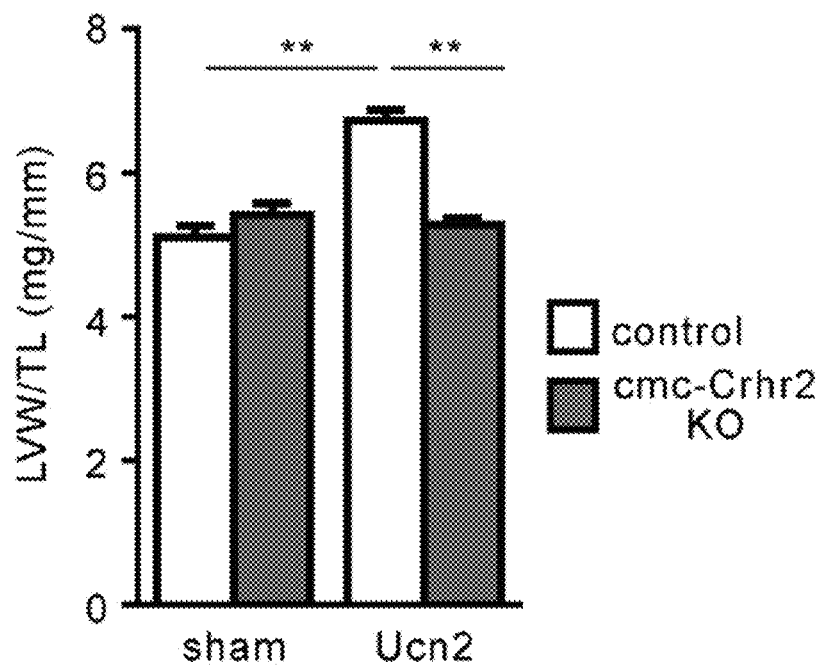
{Figure 12}
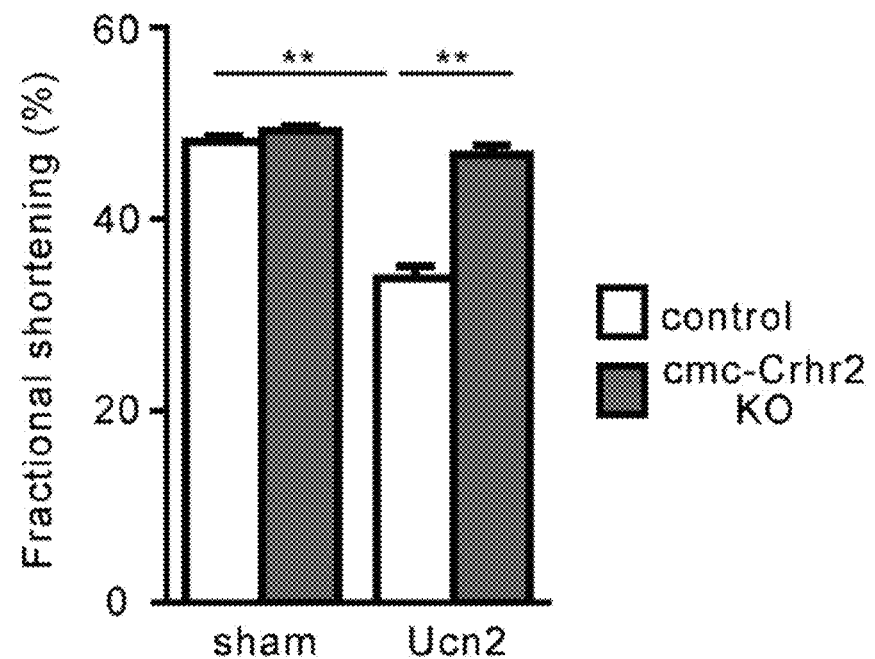
{Figure 13}

{Figure 14}
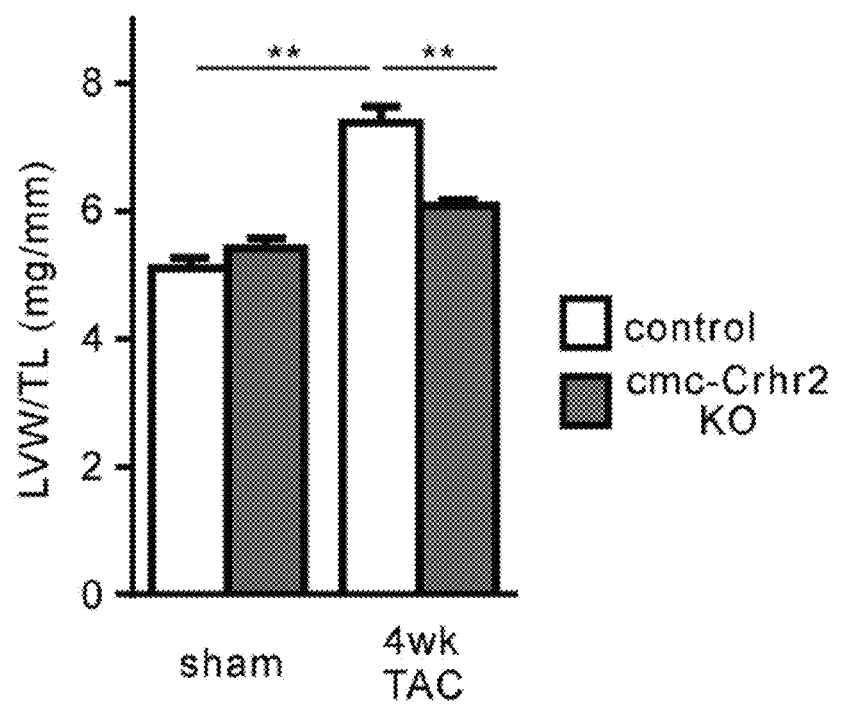

{Figure 15}
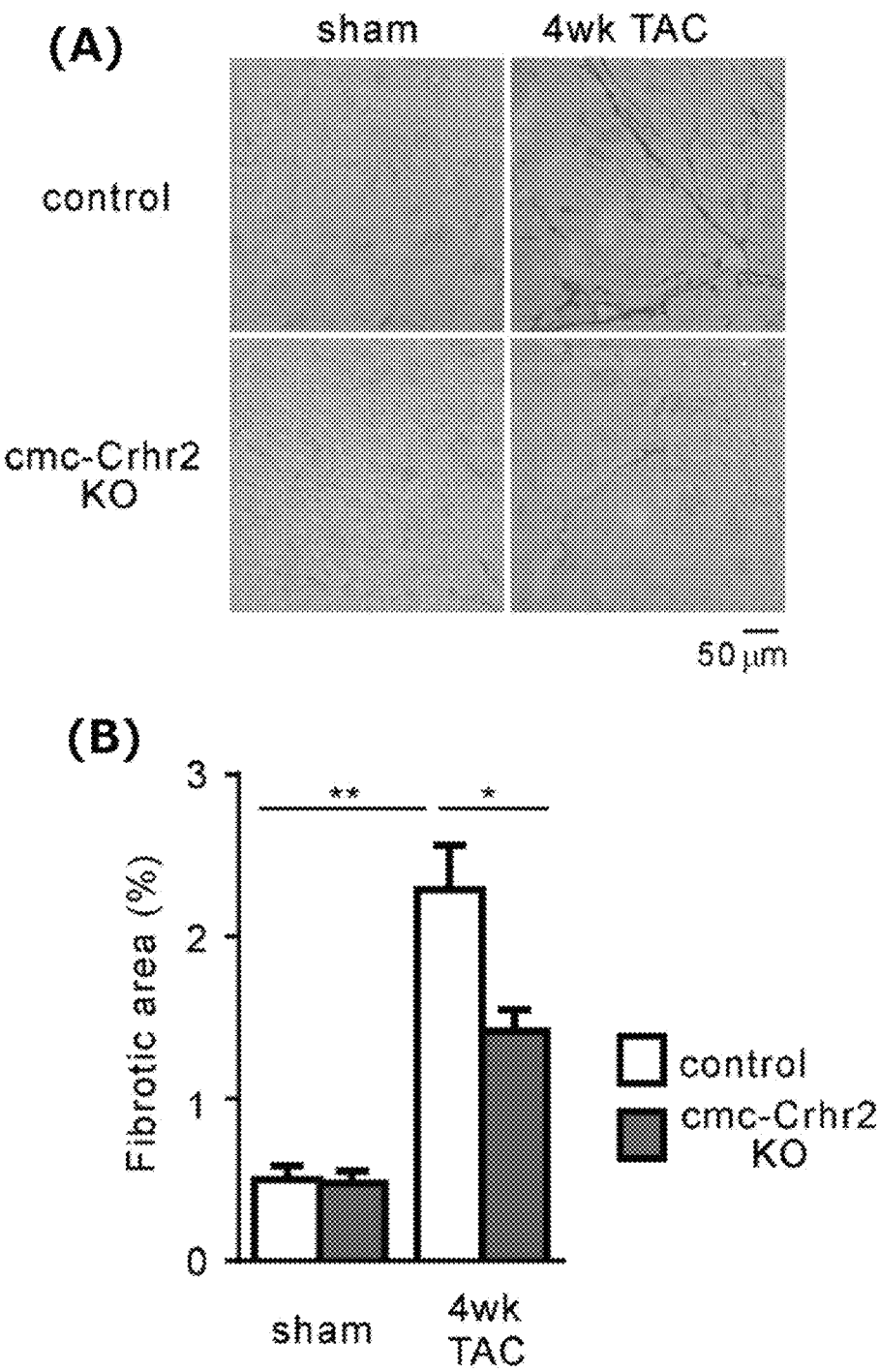

{Figure 16}
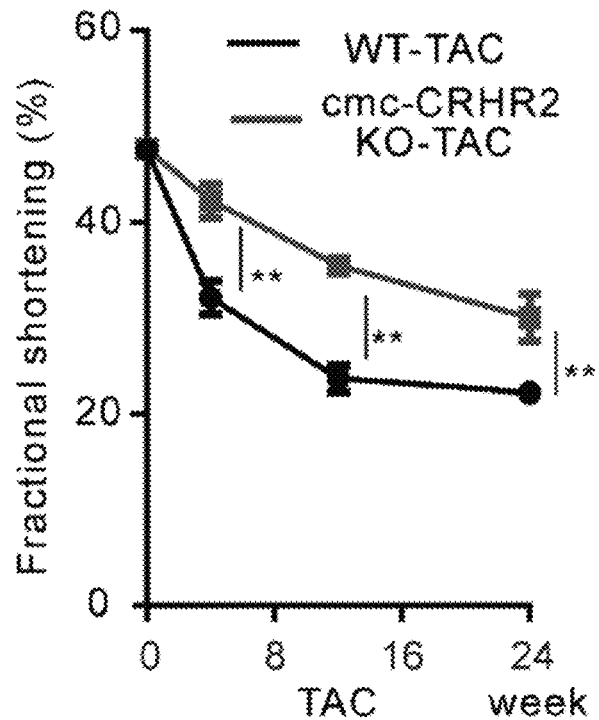
{Figure 17}
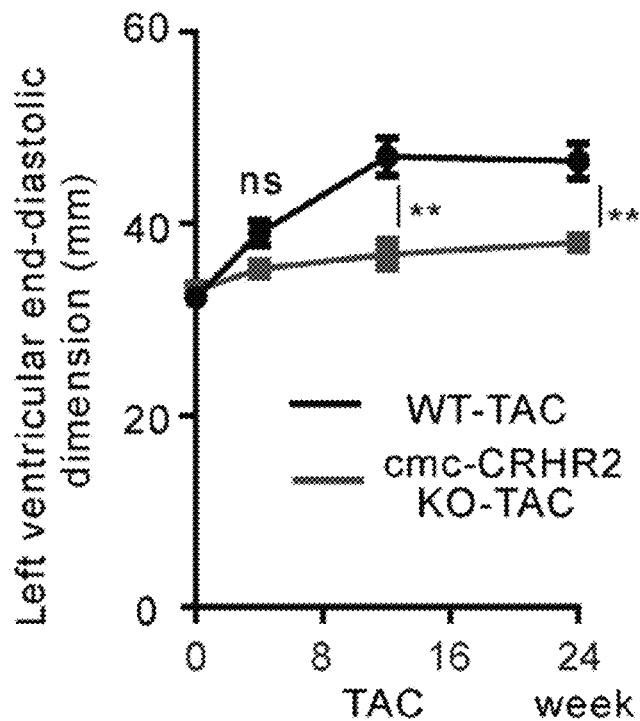

{Figure 18}
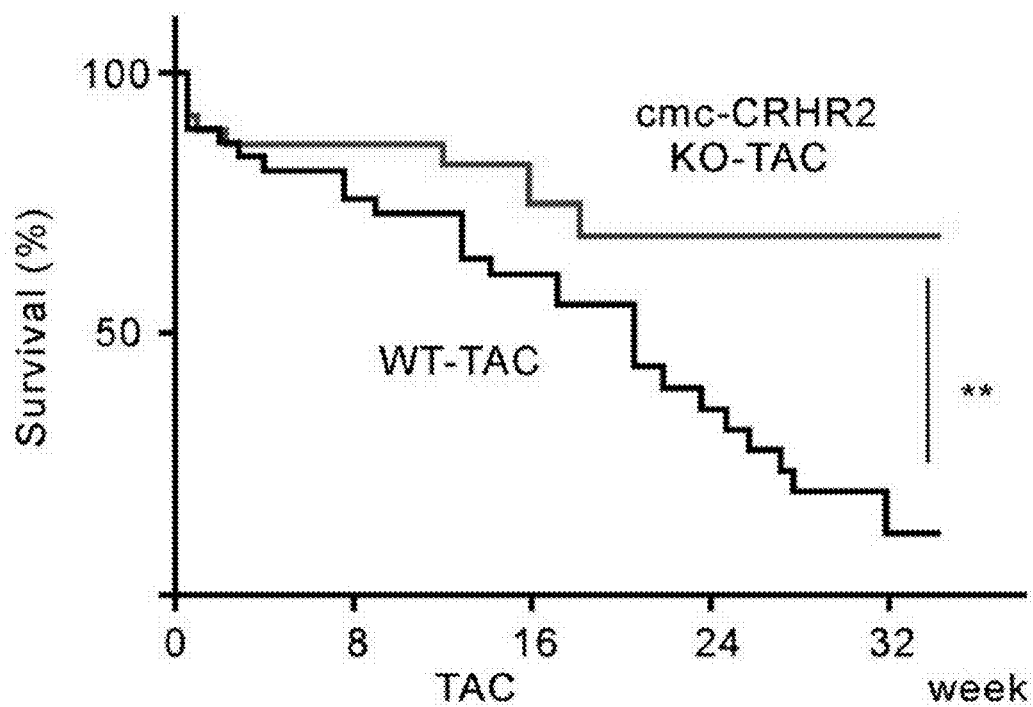
{Figure 19}
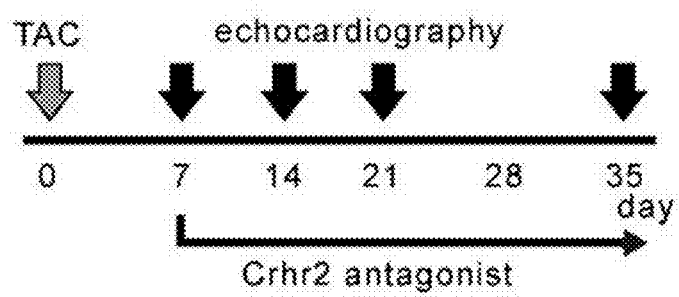

{Figure 20}
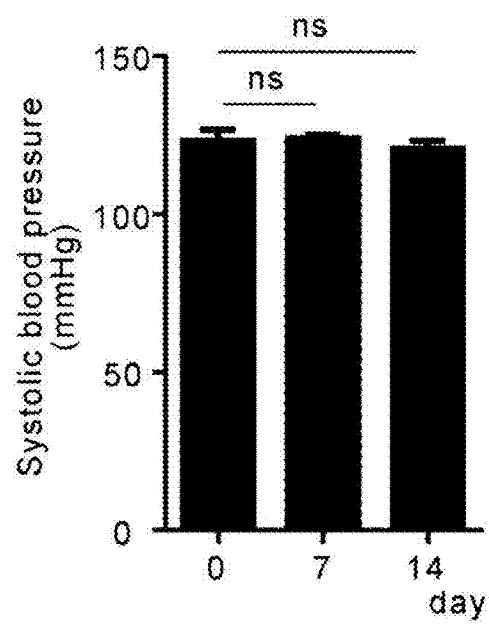
{Figure 21}
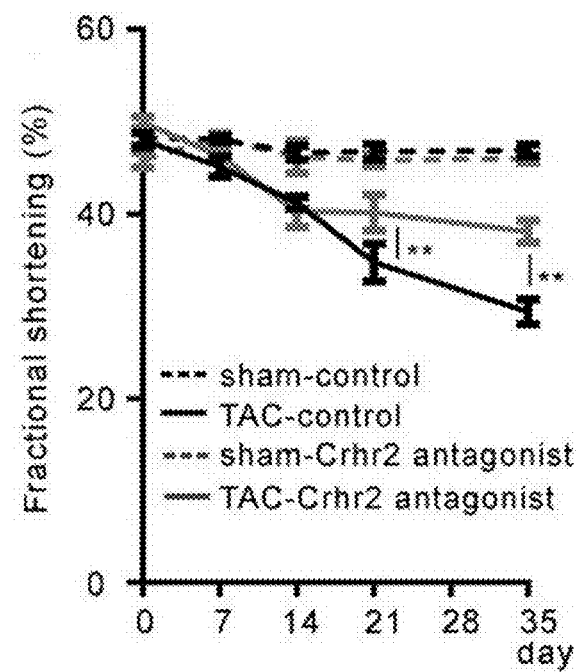

{Figure 22}
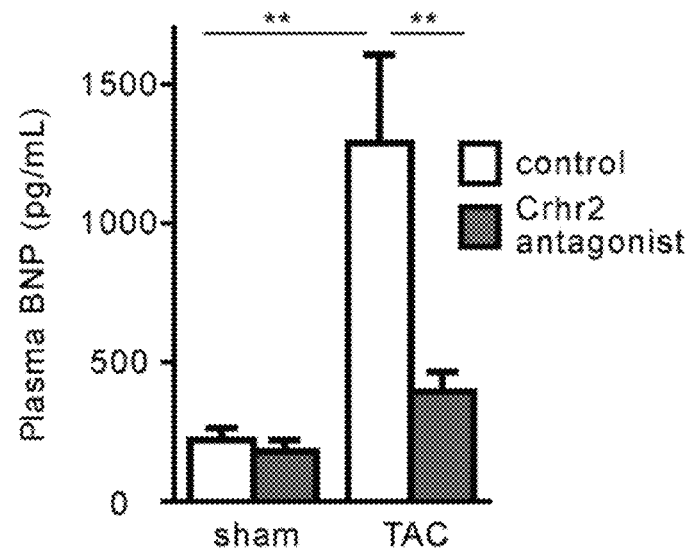
{Figure 23}
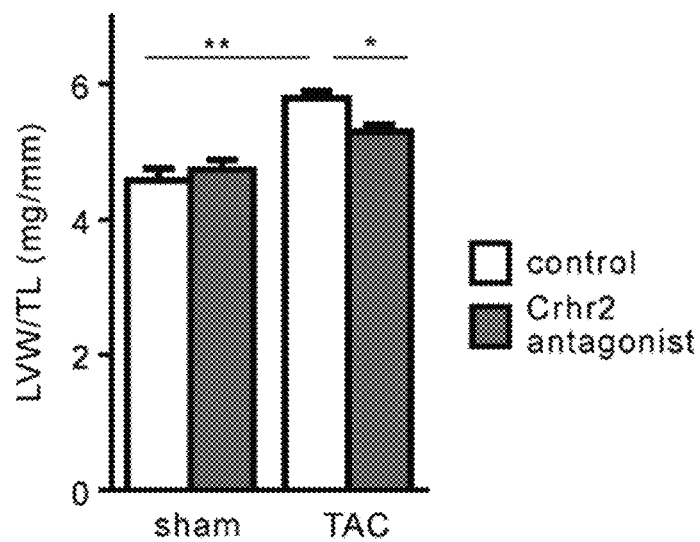

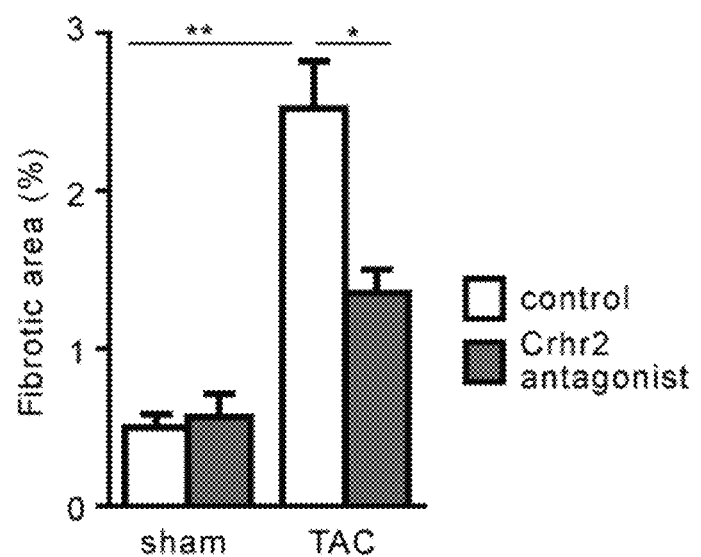
{Figure 24}

METHOD FOR PREVENTING OR TREATING HEART FAILURE BY ADMINISTERING A MEDICAMENT CONTAINING AN ANTAGONIST OF CORTICOTROPIN RELEASING HORMONE RECEPTOR 2 (CRHR2)

TECHNICAL FIELD

The present invention relates to a medicament for preventing or treating heart failure. More specifically, the present invention relates to a medicament for preventing or treating heart failure wherein the medicament contains an antagonist of the corticotropin releasing hormone receptor 2 as an active ingredient.

BACKGROUND ART

The number of heart failure patients is very large since the number of patients with heart failure in the United States is about 6 million (American College of Cardiology, 2010) and the number of patients with heart disease in Japan is 1.7 million (Ministry of Health, Labor and Welfare, 2014). Patients with heart failure are restricted in their daily lives due to symptoms of heart failure such as short of breath and palpitations, and in particular elderly patients have difficulty in going out of doors due to symptoms of heart failure and often cannot receive adequate social services including medical care. Especially in Japan which is facing an unprecedented aging society, the development of treatment for heart failure is expected to lead to improvement of the quality of life of patients suffering from heart failure.

Heart failure, which is a common cardiovascular disease with poor prognosis, develops when the heart is unable to pump blood for maintaining tissue perfusion. Despite improvements in the treatment of cardiovascular diseases such as coronary heart disease and hypertension, the prognosis of heart failure is still poor. Several mechanisms contribute to the development of heart failure after valve disease, cardiomyopathy or myocardial infarction. In most cases, cardiac remodeling develops in response to environmental demands and various stimuli such as hormonal activation and hypertension inducing cardiac hypertrophy. Hypertrophic growth is a major mechanism to reduce stress on the ventricular wall. However, the heart becomes uncompensable under long-term stress, resulting in causing heart failure.

All cells possess transmembrane signaling systems responsive to extracellular stimuli. G protein-coupled receptors (GPCRs) are the largest superfamily of cell surface receptors and are involved in many physiological and pathological processes. GPCR-mediated signaling is implicated in various diseases, including metabolic, immunological, and neurodegenerative diseases, as well as cancer and infection diseases. Therefore, GPCRs are considered to be attractive drug targets.

In the heart, GPCRs regulate cardiac function in response to extracellular stimuli such as catecholamines and angiotensin II, and are involved in cardiac dysfunction and fibrosis. GPCR inhibitors are widely used for treating patients with heart failure (Non Patent Literature 1 and 2). The heart expresses several GPCRs, but only β adrenergic receptor inhibitors and angiotensin II receptor inhibitors are clinically used as a long-term treatment for patients with chronic heart failure. Despite these available therapies, the mortality rate and the hospitalization rate have remained relatively high for over a decade, and it is suggested that additional unknown factors may also be involved in the pathophysiology (Non Patent Literature 3).

CITATION LIST

Non Patent Literature

{PTL 1} Kang, M., K. Y. Chung, and J. W. Walker. 2007. G-protein coupled receptor signaling in myocardium: not for the faint of heart. Physiology (Bethesda). 22:174-184. http://dx.doi.org/10.1152/physiol.00051.2006

{PTL 2} Capote, L. A., R. Mendez Perez, and A. Lymperopoulos. 2015. GPCR signaling and cardiac function. Eur. J. Pharmacol. 763(Pt B):143-148. http://dx.doi.org/10.1016/j.ejphar.2015.05.019

{PTL 3} Tamargo, J., and J. López-Sendón. 2011. Novel therapeutic targets for the treatment of heart failure. Nat. Rev. Drug Discov. 10:536-555. http://dx.doi.org/10.1038/nrd3431

SUMMARY OF INVENTION

Technical Problem

Treatment of chronic heart failure has no remarkable progress since the 1980s and the number of heart failure patients has continued increasing worldwide even with existing drugs. Accordingly, it is an object of the present invention to provide a novel medicament for preventing or treating heart failure, and a method for selecting a heart failure patient effective for treatment with the said medicament. It is another object of the present invention to provide a method of screening drugs for preventing or treating heart failure.

Solution to Problem

In order to solve the above problems, the present invention includes each of the following inventions.

[1] A medicament for preventing or treating heart failure containing an antagonist of the corticotropin releasing hormone receptor 2 as an active ingredient.

[2] The medicament according to the above [1], wherein the heart failure is chronic heart failure.

[3] A method for selecting a subject effective for treatment with the medicament according to the above [1] or [2], comprising the steps of:
  measuring the serum concentration of the corticotropin releasing hormone receptor 2 agonist in a subject; and
  selecting a subject whose measured value is higher than the reference value.

[4] A method of screening drugs for preventing or treating heart failure, comprising the steps of:
  selecting a test substance capable of inhibiting the binding of a corticotropin releasing hormone receptor 2 to its ligand; or
  selecting a test substance capable of inhibiting the intracellular signal transduction caused by the binding of a corticotropin releasing hormone receptor 2 to its ligand.

[5] Use of an antagonist of the corticotropin releasing hormone receptor 2 for manufacturing a medicament for preventing or treating heart failure.

[6] An antagonist of the corticotropin releasing hormone receptor 2 for use in preventing or treating heart failure.

[7] A method for preventing or treating heart failure comprising a step of administering to a mammal an effective amount of the medicament according to the above [1] or [2].

Advantageous Effects of Invention

According to the present invention, it is possible to provide a novel medicament for preventing or treating heart failure, and a method for selecting a heart failure patient effective for treatment with the said medicament. By administering the medicament of the present invention to the patient selected by the method of the present invention, the therapeutic effect of heart failure can be remarkably improved. In addition, the drug selected by the screening method of the present invention is useful as an active ingredient of a medicament for preventing or treating heart failure.

BRIEF DESCRIPTION OF DRAWINGS

FIG. 1 shows the results for quantitative RT-PCR analysis of expression of G protein-coupled receptor (GPCR) gene in adult mouse cardiomyocytes 2 wk after transverse aortic constriction (TAC)

FIG. 2 shows the results for analyzing the expression of Crhr2, Adrb1 and Ptger1 in adult mouse cardiomyocytes 2 wk after TAC or sham procedure (sham), wherein (A) shows the results for measuring the protein expression level by Western blotting, and (B) shows the results for measuring the mRNA expression level by quantitative RT-PCR.

FIG. 3 shows the results for measuring plasma Ucn2 concentrations in adult mouse 2 wk after TAC or sham procedure (sham).

FIG. 4 shows the results for detection of expression of Crhr2 in various human tissues by Western blotting.

FIG. 5 shows the results for measuring plasma Ucn2 concentrations 4 wk after continuous infusion of Ucn2 (25, 50 or 100 ng/g/day) or vehicle through an osmotic pump implanted subcutaneously into mouse.

FIG. 6 shows the photograph of the heart 4 wk after continuous infusion of Ucn2 (100 ng/g/day) or vehicle (sham) through an osmotic pump implanted subcutaneously into mouse.

FIG. 7 shows the left ventricular weight/tibia length ratio 4 wk after continuous infusion of Ucn2 (25, 50 or 100 ng/g/day) or vehicle through an osmotic pump implanted subcutaneously into mouse.

FIG. 8 shows the left ventricular fractional shortening rate 4 wk after continuous infusion of Ucn2 (100 ng/g/day) or vehicle (sham) through an osmotic pump implanted subcutaneously into mouse.

FIG. 9 shows the systolic blood pressure 4 wk after continuous infusion of Ucn2 (100 ng/g/day) or vehicle (sham) through an osmotic pump implanted subcutaneously into mouse.

FIG. 10 shows the brain natriuretic peptide (BNP) 4 wk after continuous infusion of Ucn2 (100 ng/g/day) or vehicle (sham) through an osmotic pump implanted subcutaneously into mouse.

FIG. 11 shows the results for comparing expression of Crhr2 in cardiomyocytes of cardiomyocyte-specific Crhr2 knockout mice with expression of Crhr2 in cardiomyocytes of Cre$^-$/tamoxifen$^-$, Cre$^+$/tamoxifen$^-$ and Cre$^-$/tamoxifen$^+$ mice.

FIG. 12 shows the left ventricular weight/tibia length ratio 4 wk after continuous infusion of Ucn2 (100 ng/g/day) or vehicle (sham) through an osmotic pump implanted subcutaneously into cardiomyocyte-specific Crhr2 knockout mice and control mice ($\alpha$MHC-CreERT2$^{+/-}$Crhr2$^{wt/wt}$).

FIG. 13 shows the left ventricular fractional shortening rate 4 wk after continuous infusion of Ucn2 (100 ng/g/day) or vehicle (sham) through an osmotic pump implanted subcutaneously into cardiomyocyte-specific Crhr2 knockout mice and control mice ($\alpha$MHC-CreERT2$^{+/-}$Crhr2$^{wt/wt}$).

FIG. 14 shows the left ventricular weight/tibia length ratio in cardiomyocyte-specific Crhr2 knockout mice and control mice ($\alpha$MHC-CreERT2$^{+/-}$Crhr2$^{wt/wt}$) 4 wk after TAC or sham procedure (sham).

FIG. 15 shows the results for the observation of left ventricular fibrosis in cardiomyocyte-specific Crhr2 knockout mice and control mice ($\alpha$MHC-CreERT2$^{+/-}$Crhr2$^{wt/wt}$) 4 wk after TAC or sham procedure, wherein (A) shows the results for an observation image of Picro-Sirius red stained sample, and (B) shows the results of quantifying the fibrosis area.

FIG. 16 shows a time course in left ventricular fractional shortening rate in cardiomyocyte-specific Crhr2 knockout mice and wild type mice subjected to TAC procedure.

FIG. 17 shows a time course in left ventricular end-diastolic diameters in cardiomyocyte-specific Crhr2 knockout mice and wild type mice subjected to TAC procedure.

FIG. 18 shows the survival rate in cardiomyocyte-specific Crhr2 knockout mice and wild type mice subjected to TAC procedure.

FIG. 19 shows the experimental plan for confirming the effect of Crhr2 antagonist on pressure-induced heart failure.

FIG. 20 shows a time course of the systolic blood pressure in mice implanted an osmotic pump subcutaneously with continuous infusion of a Crhr2 antagonist (100 ng/g/day) 1 wk after TAC procedure.

FIG. 21 shows a time course of left ventricular fractional shortening in mice implanted an osmotic pump subcutaneously with continuous infusion of a Crhr2 antagonist (100 ng/g/day) 1 wk after TAC or sham procedure (TAC-Crhr2 antagonist and sham-Crhr2 antagonist, respectively) and in mice implanted an osmotic pump subcutaneously with continuous infusion of vehicle 1 wk after TAC or sham procedure (TAC-control and sham-control, respectively).

FIG. 22 shows the blood brain natriuretic peptide (BNP) concentration on the 35 d after the same procedure of four types of mice as in FIG. 21.

FIG. 23 shows the left ventricular weight/tibia length ratio on the 35 d after the same procedure of four types of mice as in FIG. 21.

FIG. 24 shows the fibrosis area on the 35 d after the same procedure of four types of mice as in FIG. 21.

DESCRIPTION OF EMBODIMENTS

The inventors of the present invention found that the corticotropin releasing hormone receptor 2 (hereinafter referred to as "Crhr2"), which is one type of G protein-coupled receptors (GPCR), was high expression in the heart of a heart failure model mice, and that the development of heart failure was suppressed in Crhr2-deficient heart failure model mice. Furthermore, it was found that heart failure was significantly improved when Crhr2 antagonist was administered to heart failure model mice. In addition, when the blood concentrations of Crhr2 agonist (urocortin 2) in healthy volunteers and patients with heart failure were measured, it was found that blood concentrations of Crhr2 agonist increased in patients with heart failure.

Published Japanese Translation of PCT International Application No. 2012-508014 discloses that administration of a Crhr2 peptide agonist is effective for treatment of heart failure, diabetes and the like. On the contrary, the present invention has found that a Crhr2 antagonist is effective for the prevention or treatment of heart failure. This is exact opposite to the invention disclosed in Japanese Translation of PCT International Application No. 2012-508014, which means the present invention is unexpected.

[Medicament for Preventing or Treating Heart Failure]

The present invention provides a medicament for preventing or treating heart failure comprising a Crhr2 antagonist as an active ingredient. Heart failure is a condition that occurs when the heart can no longer supply enough blood to meet the metabolic needs of the body tissues due to impairment of the pump function of the heart and is classified as acute heart failure and chronic heart failure, according to the onset time. The medicament of the present invention can be used for treatment of both chronic heart failure and acute heart failure and is preferably used for treating chronic heart failure.

Crhr2 antagonist means a compound capable of inhibiting the intracellular signal transduction caused by ligand binding to Crhr2. Such a compound may be a naturally occurring compound or an artificially synthesized compound. Further, it may be a low molecular weight compound or a polymer compound such as a protein.

As the Crhr2 antagonist, a compound which inhibits the binding of Crhr2 to its ligand can be preferably used. Specifically, examples of such compounds include an antibody or peptide that specifically binds to Crhr2, an antibody or peptide that specifically binds to a ligand of Crhr2, and the like. The ligand of Crhr2 includes, for example, urocortin 2 (hereinafter referred to as "Ucn2"). The antibody may be a polyclonal antibody or a monoclonal antibody. The antibody may also be an intact antibody molecule or it may be an antibody fragment (e.g., Fab, F (Ab') 2, Fab', Fv, scFv etc.) that can specifically bind to the antigen. The antibody is preferably a human chimeric antibody or a humanized antibody. Preferred embodiments of antibodies capable of inhibiting the intracellular signal transduction caused by binding of ligand to Crhr2 include antibodies capable of inhibiting the intracellular signal transduction by binding to Crhr2 (anti-Crhr2 neutralizing antibody), or antibodies capable of inhibiting the intracellular signal transduction by binding to Ucn2 (anti-Ucn2 neutralizing antibody).

The antibody that specifically binds to Crhr2 or Ucn2 can be prepared by a known method using Crhr2 or a fragment thereof, or Ucn2 or a fragment thereof, respectively, as an antigen. Information regarding the nucleotide and amino acid sequences of the genes encoding Crhr2 and Ucn2 proteins of major mammals including humans can be obtained from known databases (e.g., DDBJ/GenBank/EMBL), and recombinant Crhr2 or recombinant Ucn2 prepared using these genetic information and known genetic recombination technology can be used as the antigen. The peptide that specifically binds to Crhr2 can be prepared by a solid phase synthesis method (e.g., the Fmoc method and the Boc method) or a liquid phase synthesis method according to a known ordinary peptide synthesis protocol.

In the present invention, as a Crhr2 antagonist, a low molecular weight compound which suppresses or blocks intracellular signal transduction caused by binding of ligand to Crhr2 can be preferably used. As such a low molecular weight compound, a low molecular weight compound which interacts with Crhr2 to inhibit binding of the ligand to Crhr2 includes, for example, the compounds disclosed in WO9808821 such as (9aR, 13aR)-N-(2-aminoethyl)-15-oxo-9a,10,11,12,13,13a,14,15-octahydro-9H-benzo[7,8]quinazolino[5,4-ab]phenazine-8-carboxamide (BMCL, 765-770, 1999); the compounds disclosed in WO2011092293 such as trans-5-chloro-N-[4-(3-ethyl-2-oxo-2,3-dihydrobenzimidazol-1-ylmethyl)-cyclohexyl]-2-methyl-nicotinamide; the compounds disclosed in WO2011095450 such as trans-2-chloro-N-(4-{[4-(2-chloro-4-methoxy-phenyl)-5-methyl-1H-pyrazol-3-ylamino]-methyl}-cyclohexyl)-5-trifluoromethyl-benzamide; the compounds disclosed in JP-A No. 11-180958 such as 4-(4,5-diphenyl-1H-imidazol-2-yl)-N,N-dimethylaniline and the like.

In the present invention, low molecular weight compounds reported as low molecular compounds of corticotropin releasing hormone receptor (Crhr) antagonist, for example, WO9413643, WO9413644, WO9413661, WO9413676, WO9413677, WO9533727, WO9533750, WO9534563, EP691128, EP576350, EP659747, WO9510506, WO9639400, WO9635689, WO9808846, WO02088095, WO03008412, U.S. Pat. No. 5,063,245 and the like can be used. In addition, the technical idea of the present invention also includes Crhr2 antagonists that will be disclosed in the future, and these can also be preferably used.

The medicament of the present invention can be prepared in the usual manner in a dosage form containing a Crhr2 antagonist as an active ingredient. For example, the dosage form can be an oral preparation and the examples include solid or liquid preparations, specifically tablets (including sugar-coated tablets and film-coated tablets), pills, granules, powders, capsules (including soft capsules), syrups, emulsions, suspensions, etc. These preparations can be produced by known methods and contain one or more carriers, diluents or excipients commonly used in the field of pharmaceutical formulation. For example, carriers or excipients used for tablets include lactose, starch, sucrose and magnesium stearate. The dosage form may be a parenteral preparation and the examples include injections and suppositories. The injections include an intravenous injection, a subcutaneous injection, an intracutaneous injection, an intramuscular injection, an intravenous infusion and an intraarticular injection. These injections are prepared according to known methods, for example, by dissolving, suspending or emulsifying the active ingredient in a sterile aqueous or oily liquid commonly used for injections. As an aqueous liquid for injection, for example, physiological saline, an isotonic solution containing glucose and an auxiliary substance, or the like can be used, optionally together with a suitable solubilizer such as alcohols (e.g., ethanol etc.), polyalcohols (e.g., propylene glycol, polyethylene glycol, etc.) and non-ionic surfactants (e.g., polysorbate 80, HCO-50, etc.). As an oily liquid, for example, sesame oil, soybean oil or the like can be used, optionally together with a solubilizer such as benzyl benzoate and benzyl alcohol. Suppositories for rectal administration are prepared by mixing the active ingredient with a commonly used base for suppositories.

The pharmaceutical preparations that can be obtained in the above manner are safe and less toxic, and therefore can be administered orally or parenterally to, for example, humans and other mammals (e.g., rats, mice, rabbits, sheep, pigs, cows, cats, dogs, monkeys, etc.).

The medicament of the present invention can comprise 0.001 to 50% by mass, preferably 0.01 to 10% by mass, and more preferably 0.1 to 1% by mass of the active ingredient. The dose of the medicament of the present invention is appropriately determined in consideration of the purpose, the type and severity of the disease, the age, body weight, sex and medical history of the patient, the kind of the active ingredient, etc. In the case where the subject is an average human weighing about 65 to 70 kg, the daily dose is preferably about 0.02 to 4000 mg, and more preferably about 0.1 to 200 mg. The total daily dose may be given as a single dose or in divided doses.

[Method for Selecting Subjects Effective for Medical Treatment with the Medicament of the Present Invention]

The present invention provides a method for selecting a subject effective for treatment with the medicament of the present invention. The selection method of the present invention may be any method as long as it includes a step of measuring the blood concentration of Crhr2 agonist in a subject and a step of selecting a subject whose measured value is higher than the reference value. The subjects are not limited to those who have already undergone diagnosis of heart failure and may be those suspected of heart failure. Those suspected of heart failure include those with subjective symptoms of shortness of breath and swelling.

Crhr2 agonists include Ucn2, Urocortin1 (Ucn1), Urocortin3 (Ucn3), corticotropin releasing hormone (Crh), Sauvagine, Crh peptide family including related peptides, and the like. Ucn2 is more preferable.

In the case where the Crhr2 agonist is Ucn2, blood concentration can be measured, for example, using plasma separated from the blood of the subject as a sample, by means of an immunological method such as ELISA.

As the reference value, the blood concentration of Ucn2 in a healthy subject sample measured at the same time can be used. In addition, an arbitrary reference value may be set based on the accumulated measurement value of the blood concentration of Ucn2 in healthy subject samples (healthy person accumulation data). Preferably, a reference value set based on accumulated data of healthy subjects is used. For healthy subjects, adults not suffering from chronic diseases are preferred, regardless of gender, and in addition not aged adults are more preferable.

When the measured value of Ucn2 blood concentration in the subject is higher than the reference value, it can be determined that the said subject is a subject effective for treatment with the medicament of the present invention. For example, when the measured value is twice or higher than the reference value, it can be determined that the said subject is a subject effective for treatment with the medicament of the present invention, and when the measured value is three times or higher than the reference value, it can be determined that the said subject is a subject effective for treatment with the medicament of the present invention. The higher the measured value is from the reference value, the higher the therapeutic effect of the medicament of the present invention can be expected.

[Screening Method]

The present invention provides a method of screening drugs for preventing or treating heart failure. The screening method of the present invention comprises the step of selecting a test substance capable of inhibiting the binding of Crhr2 to its ligand or the test substance capable of inhibiting the intracellular signal transduction caused by the binding of Crhr2 to its ligand. The test substance selected by the screening method of the present invention is a drug useful as an active ingredient of a medicament for preventing or treating heart failure.

The test substances to be screened include nucleic acids, peptides, proteins, non-peptidic compounds, synthetic compounds, fermentation products, cell extracts, cell culture supernatants, plant extracts, mammalian tissue extracts and plasma, etc., but are not limited to these examples. The test substances may be novel or known substances. These test substances may be in the form of a salt. The salt is composed of the test substance with a physiologically acceptable acid or base.

For the selection of the substance capable of inhibiting the binding of Crhr2 to its ligand, the screening method can comprise, for example, the following steps:
  bringing a test substance into contact with Crhr2 and its ligand;
  assessing binding of Crhr2 to its ligand; and
  selecting the test substance capable of inhibiting the binding of Crhr2 to its ligand.

Ucn2 can be used as a ligand for Crhr2. The Crhr2 and Ucn2 to be used may be native or recombinant proteins. Crhr2 expressing cells may also be used.

The method for bringing the test substance into contact with Crhr2 and Ucn2 is not particularly limited. For example, a reaction system containing Crhr2 and Ucn2 is prepared, and the test substance is added thereto. The contact time and temperature are not particularly limited and can be selected as appropriate. The method for assessing Ucn2 binding to Crhr2 is not particularly limited, and a known method for determining the level of Ucn2 binding to Crhr2 can be selected as appropriate. For example, ELISA, fluorescence polarization, flow cytometry, surface plasmon resonance, and the like can be preferably used. In an exemplary method using ELISA, either Crhr2 or Ucn2 is immobilized, the other one and the test substance are added thereto so that the reaction proceeds, and the level of Ucn2 binding to Crhr2 is determined with the use of appropriate primary and secondary antibodies.

When the level of Ucn2 binding to Crhr2 after the contact with the test substance is reduced as compared with that in the control group which is not in contact with the test substance, the test substance can be determined as a desired substance. The selection criterion for the reduction of the level of Ucn2 binding to Crhr2 is not particularly limited, for example, the desired substance is a substance capable of reducing the level of Ucn2 binding to Crhr2 to 50% or less, or 25% or less of that in the absence of contact with the test substance.

For the selection of the substance capable of inhibiting the intracellular signal transduction caused by the binding of Crhr2 to its ligand, the screening method can comprise, for example, the following steps:
  adding a test substance to a culture system containing Crhr2 expressing cells and its ligand;
  assessing the signal transduction state downstream of Crhr2; and
  selecting a substance capable of inhibiting the intracellular signal transduction caused by the binding of Crhr2 to its ligand.

Ucn2 can be used as a ligand for Crhr2.

Crhr2 expressing cells may be endogenous cells expressing Crhr2 or cells expressing recombinant Crhr2. For example, HEK 293 cells co-transfected with a Crhr2 expression vector and a reporter gene-linked vector downstream of a cAMP response element (CRE: cAMP-responsive element) can be used. When Crhr2 expressing cells which a reporter gene is introduced into are used, the signal transduction state downstream of Crhr2 can be assessed by measuring the expression level of the reporter gene. The reporter gene is not particularly limited as long as it is generally used, and examples thereof include genes encoding luciferase, β-galactosidase, β-glucuronidase, chloramphenicol acetyltransferase, alkaline phosphatase, peroxidase, green fluorescent protein (GFP) and the like.

When the expression level of the reporter gene after the contact with the test substance is reduced as compared with that in the control group which is not in contact with the test substance, the test substance can be determined as a desired substance. The selection criterion for the reduction of the expression level of the reporter gene is not particularly limited, and for example, the desired substance is a substance capable of reducing the expression level of the reporter gene to 50% or less, or 25% or less of that in the absence of contact with the test substance.

EXAMPLES

Hereinafter, the present invention will be illustrated in detail by examples, but the present invention is not limited thereto.

<Materials and Methods>

(1) Materials

Antibodies to anti-Crhr2 antibody (sc-20550), anti-β-actin antibody (sc-47778), anti-Adrb1 antibody (sc-568), and anti-Ptger1 antibody (sc-22648), were obtained from Santa Cruz Biotechnology, Inc. Human tissue samples were obtained from BioChain.

(2) Western Blotting

Cell and tissue samples were lysed in RIPA buffer (Wako) containing a protease inhibitor mixture and phosphatase inhibitor mixture (Roche). Protein concentrations were measured using a BCA protein assay (Thermo Fisher Scientific). Equal amounts of proteins were resolved by SDS-PAGE and transferred onto a PVDF membrane. ECL or ECL plus western blotting detection kits (GE Healthcare) were used for signal detection.

(3) Isolation of Adult Mouse Ventricular Cardiomyocytes

Cardiomyocytes were isolated as described in the literature, Wolska and Solaro, Am. J. Physiol. 271:H1250-H1255, 1996. At the setout, mice were heparinized (5,000 IU/kg) and anesthetized with 50 mg/kg sodium pentobarbital. Hearts were quickly removed, cannulated from the aorta with a blunted 24-gauge needle, and then connected to a perfusion apparatus for retrograde perfusion of the coronary arteries with perfusion buffer (135 mM NaCl, 4.0 mM KCl, 0.33 mM $NaH_2PO_4$, 1.0 mM $MgCl_2$, 10 mM Hepes, 5 mM taurine, 10 mM 2,3-butanedione monoxime, and 10 mM glucose, pH 7.4) for 3 min (5 ml/min), and then with enzyme buffer, which is the perfusion buffer supplemented with 0.4 mg/ml collagenase D (Roche), 0.5 mg/ml collagenase B (Roche), and 0.06 mg/ml protease XIV (Sigma-Aldrich), for 10 min. After the heart was removed from the perfusion apparatus, atria were removed, ventricles were cut and separated into small pieces gently with forceps, and pipetted several times in perfusion buffer containing 5% BSA. Cells were plated in MEM (Thermo Fisher Scientific) containing 2.0 mM l-glutamine, 10 mM 2,3-butanedione monoxime, 10 µg/ml insulin, 5.5 µg/ml transferrin, 5.0 ng/ml selenium, and 0.1% BSA for 1 h, at which point media was removed and adherent cells were resuspended in BSA-free culture medium until use, generally within 1-2 h.

(4) mRNA Expression Analysis

To analyze GPCR expression, RNA was extracted from adult mouse cardiomyocytes. An RNeasy Mini kit (QIA GEN) was used for RNA extraction according to the manufacturer's protocol. A QuantiTect Reverse Transcription kit (QIA GEN) was used for reverse-transcription. Quantification was performed using a LightCycler 480 Probe Master System (Roche) with primers specific to each GPCR. Genomic DNA from mouse tails was used as a universal standard to calculate gene copy number per ng of RNA (Yun et al., 2006, Nucleic Acids Res. 34:e85).

(5) Tamoxifen-Inducible, Cardiomyocyte-Specific Crhr2 Knockout Mice (cmc-Crhr2-KO)

$Crhr2^{tm1a(KOMP)Wtsi}$ mice on a C57BL/6 background were generated by the Knock Out Mice Program (KOMP) at the University of California Davis (Davis, Calif.) and Children's Hospital Oakland Research Institute (Oakland, Calif.). $Crhr2^{tm1a(KOMP)Wtsi}$ mice were bred with mice expressing Flp recombinase to obtain Crhr2 conditional KO mice ($Crhr2^{flox/flox}$ mice). $Crhr2^{flox/flox}$ mice were backcrossed at least 10 times to wild-type C57BL/6 genetic background mice. Tamoxifen-inducible, cardiomyocyte-specific Crhr2 knockout mice (cmc-Crhr2-KOs) were generated by intercrossing the αMHC-CreERT2 line to $Crhr2^{flox/flox}$ mice (Takefuji et al., 2012, Circulation. 126:1972-1982). Cre-mediated recombination of floxed alleles was induced with an intraperitoneal injection of 1 mg tamoxifen dissolved in 100 µl Miglyol for 5 consecutive days. Vehicle-treated mice received Miglyol only, and αMHC-CreERT2+/−Crhr2$^{wt/wt}$ mice were used as controls. Experiments were performed 2 wk after the end of induction.

(6) Surgical Interventions: Osmotic Minipumps and Transverse Aortic Constriction (TAC; Transverse Aortic Constriction)

8-10-week-old male mice were anesthetized with 50 mg/kg sodium pentobarbital, and osmotic minipumps (Alzet) containing Ucn2 (25, 50, 100 ng/g/day; Peptide Institute) or antisauvagine-30 (100 ng/g/day; Medical & Biological Laboratories) were implanted subcutaneously in the back for 4 wk.

TAC was performed under anesthesia and intubation. The chest was opened to visualize the aortic arch. The transverse aorta was then ligated between the right innominate and left common carotid arteries against a blunted 24-G needle with a 7-0 suture. The sham procedure was identical except that the aorta was not ligated.

Transthoracic echocardiography was performed on mice anesthetized with 50 mg/kg sodium pentobarbital. The left ventricular (LV) end-systolic diameter and the LV end-diastolic diameters were measured to calculate the % LV fractional shortening (% FS) in M-mode using an *Acuson Sequoia* C-512 (Siemens) with a 15-MHz probe. Systolic blood pressure (SBP) was measured by tail cuff method with an automatic sphygmomanometer (BP98A; Saffron) while the mice were restrained.

Mouse plasma Ucn2 and BNP were quantified by a mouse Ucn2 ELISA kit (Yanaihara), and by a BNP Enzyme Immunoassay kit (RayBiotech Inc.), respectively, according to the manufacturer's instructions.

(7) Histological Analysis

Tissue samples were embedded in OCT compound (Sakura Finetek) and snap-frozen in liquid nitrogen. Left ventricular myocardium sections (6 µm slices) were stained with Picro-Sirius red with standard protocols and viewed with a BX51 microscope (Olympus). Cardiac fibrosis in 20 random images was quantified in ImageJ software.

(8) Clinical Data of Human Subjects

Blood samples were collected from patients diagnosed with NIDCM (nonischemic dilated cardiomyopathy) at Nagoya University hospital from August 2006 to November 2011. All patients showed stable disease and were hospitalized for detailed cardiac examination by laboratory analysis, echocardiography, and cardiac catheterization. NIDCM was defined as left ventricular ejection fraction (LVEF) <50% on left ventriculography and a dilated LV cavity (LV end-diastolic dimension >55 mm determined by echocardiography), in the absence of coronary heart disease, valvular heart disease, or secondary cardiac muscle disease caused by any known systemic conditions, as determined by endomyocardial biopsy. Of 52 patients, 36 (69.2%) received angiotensinconverting enzyme inhibitors or aldosterone receptor antagonists, 30 (57.7%) received β blockers, and 21 (40.4%) received mineralocorticoid receptor antagonists. Blood samples were collected from the antecubital vein of fasting patients in the morning after resting for 20 min in the supine position. Control blood samples were collected from age- and gender-matched healthy participants of a community-based cohort study without a history of metabolic, cardiovascular, or cancerous diseases. BMI was calculated as follows: BMI=weight (kg)/height (m)$^2$. Systolic blood pressure (SBP) and diastolic blood pressure (DBP) were measured with a sphygmomanometer, placed on the right arm of each subject with the appropriate cuff size. Plasma total cholesterol, creatinine, and glucose levels were measured by enzymatic methods. BNP (RayBiotech Inc.) and Ucn2 levels (USCN Life Science) were measured by ELISA.

(9) Study Approval

The clinical study protocol was approved by the Ethics Review Board of Nagoya University School of Medicine and Jichi Medical University. Written informed consent was obtained from all study subjects. All procedures of animal care and animal use in this study were approved by the Animal Ethics Review Board of Nagoya University School of Medicine.

(10) Statistical Analysis

Data are presented as the means±SEM in animal experiments and the means±SD, medians (interquartile ranges), or subject numbers (%) in human subjects. All statistical analyses for animal experiments were performed in GraphPad Prism 6. Comparisons between two groups were performed with unpaired Student's t or Chi-square tests, while those between more than two groups were done using ANOVA with Bonferroni post-hoc testing. Survival curves were analyzed with Kaplan Meyer estimators and Log-rank (Mantel-Cox) testing. Comparisons between more than two groups at different time points were performed by two-way ANOVA, followed by Bonferroni post-hoc test. Since Ucn2 showed a skewed distribution in the human studies, the variables were log-transformed before analysis, and differences were assessed using a general linear model with parameter adjustments. Significance was defined as $P<0.05$ (*, $P<0.05$; **, $P<0.01$; ns, no significant difference).

<Results>

(1) Continuous Crhr2 Activation Causes Heart Failure in Mice

A systematical search was performed to identify GPCRs expressed in cardiomyocytes and related to heart failure. For this, we performed non-biased quantitative RT-PCR (qRT-PCR) analysis to determine the gene copy number of 475 GPCRs in adult murine cardiomyocytes 2 wk after sham procedure or transverse aortic constriction (TAC). Data revealed that adult murine cardiomyocytes expressed about 80 GPCRs (5 or more copies per ng of RNA), the most abundant being Crhr2, Adrb1, Ptger1, and Gpr157 (FIG. 1). Crhr2 expression was markedly increased at the gene and protein level in the left ventricle 2 wk after TAC, whereas Adrb1 expression was decreased and Ptger1 expression was unchanged (FIGS. 2(A) and (B)). Moreover, TAC significantly increased Ucn2 levels in the blood (FIG. 3). Western blot analysis of various human tissues indicated that Crhr2 is exclusively expressed in the heart and is undetectable in other tissues (FIG. 4). Together, these results indicate that Crhr2 is highly expressed in cardiomyocytes and increases after pressure overload-induced heart failure.

Acute intravenous injection of Ucn2 has been shown to accelerate cardiac contraction (Coste et al., 2000, Nat. Genet. 24:403-409), but whether a chronic increase in plasma Ucn2 levels affects cardiac function remains unknown. To examine the effect of long-term Ucn2 up-regulation in vivo, we implanted mice with osmotic pumps that release Ucn2. After 4 wk of sustained Ucn2 infusion, blood analysis revealed that circulating Ucn2 levels were elevated similar to those observed after TAC (FIG. 5). In addition, animals showed cardiac hypertrophy with an increased left ventricular weight to tibia length ratio in a dose-dependent manner (FIGS. 6 and 7), which was accompanied by a decrease in left ventricular fractional shortening (FIG. 8) without significantly affecting systolic blood pressure (FIG. 9). Moreover, continuous Ucn2 infusion significantly increased blood levels of brain natriuretic peptide (BNP), which is secreted by cardiomyocytes in response to pressure and volume overload (FIG. 10). Collectively, these results indicate that chronic increase in plasma Ucn2 impairs cardiac function.

(2) Increased Plasma Ucn2 Levels in Patients with Heart Failure

Based on these findings, we measured plasma Ucn2 levels in 260 healthy subjects (plasma BNP <5.8 pg/ml) and 52 patients with non-ischemic dilated cardiomyopathy (plasma BNP=246.8±362 pg/ml). The clinical demographics of the patient population are shown in Table 1. Although both groups presented with similar body mass index (BMI), plasma total cholesterol, and plasma glucose levels, patients with NIDCM showed significantly lower systolic blood pressure and diastolic blood pressure, as well as significantly higher creatinine levels. Of note, patients with NIDCM exhibited significantly higher Ucn2 levels (a median 7.5-fold increase) than healthy controls, which remained significant after adjustment for all measured parameters ($P<0.01$). Thus, these data indicate that increased plasma Ucn2 is strongly associated with heart failure in humans, suggesting that Ucn2 measurement may be a novel diagnostic marker for chronic heart failure.

TABLE 1

| Parameters | Control (healthy subject) n = 260 | HF (NIDCM) n = 52 | P-value |
|---|---|---|---|
| Age, yr | 57.6 ± 10.5 | 57.4 ± 10.7 | 0.94 |
| Gender, male (%) | 140 (54%) | 28 (54%) | 1 |
| BMI, kg/m2 | 22.3 ± 2.9 | 22.7 ± 4.3 | 0.51 |
| SBP, mmHg | 133 ± 18 | 119 ± 20 | <0.01$^a$ |
| DBP, mmHg | 80 ± 11 | 73 ± 13 | <0.01$^a$ |
| Total Cholesterol, mg/dl | 203 ± 34 | 195 ± 37 | 0.13 |
| Glucose, mg/dl | 96 ± 10 | 99 ± 24 | 0.27 |
| Creatinine, mg/dl | 0.73 ± 0.15 | 0.86 ± 0.22 | <0.01$^a$ |
| Ucn2, pg/ml | 235 (54-647) | 1,755 (1,166-3,130) | <0.01$^a$ |

HF, heart failure;
DBP, diastolic blood pressure.
Data represent means ± SD, medians (interquartile ranges), or subject numbers (%).
$^a$P < 0.01 (unpaired Student's t test or Chi-square test).

(3) Attenuated Cardiac Hypertrophy, Fibrosis, and Heart Failure in Crhr2-Deficient Mice To examine the functional significance of Crhr2 in cardiomyocytes in vivo, we generated mice with tamoxifen-inducible cardiomyocyte-specific Crhr2 deficiency (cmc-Crhr2-KO) by mating αMHC-CreERT2 mice with Crhr2$^{flox/flox}$ mice. The efficiency of tamoxifen-inducible recombination was analyzed by Western blotting, which showed that Crhr2 was undetectable in cardiomyocytes isolated from tamoxifen-treated cmc-Crhr2 KO mice (FIG. 11). No differences were observed in the ratio of left ventricular weight to tibia length or cardiac function before and after tamoxifen treatment in cmc-Crhr2 KO mice (FIGS. 12 and 13). Notably, cmc-Crhr2 KO mice failed to show a Ucn2-induced hypertrophic response (FIG. 12). In addition, although 4 wk of continuous Ucn2 infusion decreased fractional shortening in control mice, this was significantly attenuated in cmc-Crhr2-KO mice (FIG. 13). These results indicate that continuous Ucn2 infusion directly affects cardiomyocytes via Crhr2.

To investigate whether cardiomyocyte-specific Crhr2 deficiency protected mice from pressure overload-induced cardiac dysfunction, we performed TAC surgeries in cmc-Crhr2 KO mice. In control mice, TAC resulted in a significant increase in cardiac hypertrophy as determined by postmortem analysis of the ratio of left ventricular weight to tibia length, whereas cmc-specific Crhr2 KO mice showed a significantly lower ratio of left ventricular weight to tibia length (FIG. 14). We also found that cmc-specific Crhr2 KO mice showed significantly less fibrosis 4 wk after TAC as determined by Picro-Sirius red staining (FIGS. 15(A) and (B)). Furthermore, cmc-Crhr2 KO mice were resistant to further deterioration of the left ventricular fractional shortening as determined by echocardiography at 4, 12, and 24 wk after TAC (FIG. 16). Ventricular dilation was also observed 12 wk after TAC in wild-type mice, but not in cmc-Crhr2 KO mice (FIG. 17). Crhr2 deficiency significantly improved mortality 8 mo after TAC (FIG. 18). Collectively, these results demonstrate that cardiomyocyte-specific Crhr2-deficient mice are resistant to pressure overload-induced cardiac dysfunction.

(4) Effect of Crhr2 Antagonist on Pressure Overload-Induced Cardiac Dysfunction

We next investigated whether treatment with the Crhr2 antagonist, antisauvagine-30 (Ruhmann et al., 1998, Proc. Natl. Acad. Sci. USA. 95:15264-15269), would attenuate the progression of established cardiac hypertrophy in mice. For this, continuous antisauvagine-30 infusion was initiated 1 wk after TAC surgery (FIG. 19). Interestingly, Crhr2 antagonist treatment protected mice from further deterioration of cardiac output without significantly affecting systolic blood pressure (FIGS. 20 and 21). These protective effects were accompanied by a strong reduction of plasma BNP, cardiac hypertrophy, and cardiac fibrosis (FIGS. 22, 23, and 24). Conversely, 4 wk of sustained Ucn2 infusion instead of antisauvagine-30 infusion initiating 1 wk after TAC surgery accelerated TAC-induced cardiac dysfunction. These results suggest that Crhr2 blockade may be a novel therapeutic approach to treat chronic heart failure.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for preventing or treating heart failure by inhibiting a corticotropin releasing hormone receptor 2-mediated intracellular signal transduction, comprising the following steps:
   (1) selecting a subject whose value of urocortin 2 is higher than a reference value, and
   (2) administering to the subject an effective amount of a medicament containing an antagonist of the corticotropin releasing hormone receptor 2 as an active ingredient,
   wherein the antagonist of the corticotropin releasing hormone receptor 2 is selected from the group consisting of cyclohexyl amide derivatives and antisauvagine-30.

* * * * *